United States Patent [19]

Schmitt et al.

[11] Patent Number: 4,565,829

[45] Date of Patent: Jan. 21, 1986

[54] FUNGICIDAL 2-THIOCYANATO-BENZAMIDES

[75] Inventors: Hans-Georg Schmitt, Leverkusen; Karlfried Wedemeyer, Cologne; Wilhelm Brandes, Leichlingen; Paul Reinecke, Leverkusen, all of Fed. Rep. of Germany

[73] Assignee: Bayer Aktiengesellschaft, Leverkusen, Fed. Rep. of Germany

[21] Appl. No.: 679,181

[22] Filed: Dec. 7, 1984

[30] Foreign Application Priority Data

Dec. 24, 1983 [DE] Fed. Rep. of Germany ....... 3347073

[51] Int. Cl.[4] ..................... A01N 47/48; C07C 161/02

[52] U.S. Cl. .................................... 514/514; 260/454

[58] Field of Search ......................... 260/454; 514/514

[56] References Cited

FOREIGN PATENT DOCUMENTS 0018100 10/1980 European Pat. Off. .

*Primary Examiner*—Dolph H. Torrence

*Attorney, Agent, or Firm*—Sprung, Horn, Kramer & Woods

[57] ABSTRACT

Novel 2-thiocyanato-benzamides of the formula

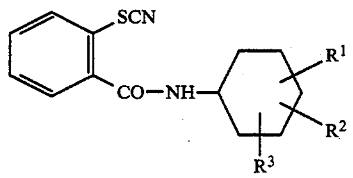

in which $R^1$, $R^2$ and $R^3$ are identical or different and represent an aliphatic radical, an arylalkyl radical which is optionally monosubstituted or polysubstituted by identical or different substituents, or a cycloalkylalkyl radical which is optionally monosubstituted or polysubstituted by identical or different substituents, or $R^1$ and $R^2$ independently of one another represent hydrogen, which possess fungicidal activity.

10 Claims, No Drawings

FUNGICIDAL 2-THIOCYANATO-BENZAMIDES

The present invention relates to new 2-thiocyanato-benzamides, a process for their preparation and their use as plant protection agents.

A number of 2-thiocyanato-benzamides, such as, for example, 2-thiocyanato-N-cyclohexyl-benzamide, and their use, for example for protecting water-containing media, such as cooling waters, paints and oil emulsions, from microbial attack, have already been disclosed (compare EP No. 0,018,100). Nothing is known of their use for combating plant diseases caused by fungi.

New 2-thiocyanato-benzamides of the formula (I)

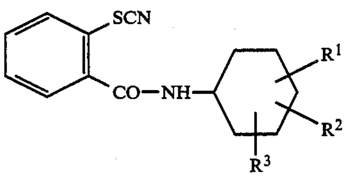

(I)

in which $R^1$, $R^2$ and $R^3$ are identical or different and represent an aliphatic radical, an arylalkyl radical which is optionally monosubstituted or polysubstituted by identical or different substituents, or a cycloalkyl-alkyl radical which is optionally monosubstituted or polysubstituted by identical or different substituents, or $R^1$ and $R^2$ independently of one another represent hydrogen, have been found.

It has furthermore been found that the 2-thiocyanato-benzamides of the formula (I)

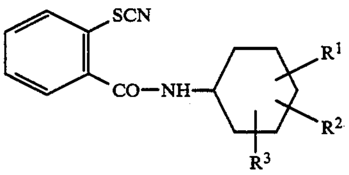

(I)

in which $R^1$, $R^2$ and $R^3$ are identical or different and represent an aliphatic radical, an arylalkyl radical which is optionally monosubstituted or polysubstituted by identical or different substituents, or a cycloalkyl-alkyl radical which is optionally monosubstituted or polysubstituted by identical or different substitutents, or $R^1$ and $R^2$ independently of one another also represent hydrogen, are obtained by a process in which 2-mercapto-benzoic acid amides of the formula (II)

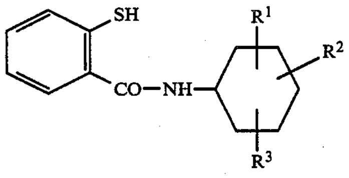

(II)

in which $R^1$, $R^2$ and $R^3$ have the abovementioned meaning, are reacted with a compound of the formula (III)

X—CN (III)

in which

X represents halogen, preferably chlorine or bromine, if appropriate in the presence of a base or an acid or basic catalyst and if appropriate in the presence of a diluent, at temperatures from −40° C. to +60° C.

The 2-thiocyanato-benzamides of the formula (I) according to the invention have powerful fungicidal properties.

Surprisingly, the compounds according to the invention exhibit a considerably more powerful action than the structurally closely related 2-thiocyanato-N-cyclohexyl-benzamide which is known from the prior art. The new compounds thus represent an enrichment of the art.

Preferred new 2-thiocyanato-benzamides of the formula (I) are those in which $R^1$, $R^2$ and $R^3$ are identical or different and represent a straight-chain, branched or cyclic alkyl radical with up to 8 carbon atoms, a phenylalkyl radical which has 1 to 4 carbon atoms, in particular 1 or 2 carbon atoms, in the alkyl radical and is optionally mono-, di-, tri-, tetra- or penta-substituted by alkyl with 1 to 4 carbon atoms, or a cycloalkyl-alkyl radical with 5 to 8 carbon atoms in the cycloalkyl part and 1 to 4, in particular 1 or 2, carbon atoms in the alkyl part, or $R^1$ and $R^2$ independently of one another represent hydrogen.

Particularly preferred 2-thiocyanato-benzamides of the formula (I) are those in which $R^1$, $R^2$ and $R^3$ are identical or different and represent straight-chain or branched alkyl with 1 to 4 carbon atoms, cycloalkyl with 5 to 8 carbon atoms, or phenylmethyl, phenylethyl, cyclohexylmethyl or cyclohexylethyl, each of which is optionally mono-, di- or tri-substituted by identical or different substituents from the group comprising methyl and ethyl, or $R^1$ and $R^2$ independently of one another represent hydrogen.

Very particularly preferred 2-thiocyanato-benzamides of the formula (I) are those in which $R^1$, $R^2$ and $R^3$ are identical or different and represent methyl, ethyl, n- or iso-propyl, cyclohexyl, or benzyl or cyclohexylmethyl, each of which is optionally mono- or di-substituted by methyl, or $R^1$ and $R^2$ independently of one another represent hydrogen.

In respect of the substituents in the cyclohexyl radical, the compounds can be pure stereoisomers or mixtures of various stereoisomers.

Besides the compounds of the formula (I) mentioned in the preparation examples, the following compounds may also be mentioned specifically:

2-Thiocyanato-benzoic acid N-(2-methyl-cyclohexyl)-amide,

2-Thiocyanato-benzoic acid N-(3,5-dimethyl-cyclohexyl)-amide,

2-Thiocyanato-benzoic acid N-(2-ethyl-cyclohexyl)-amide,

2-Thiocyanato-benzoic acid N-(3-ethyl-cyclohexyl)-amide,

2-Thiocyanato-benzoic acid N-(4-ethyl-cyclohexyl)-amide,
2-Thiocyanato-benzoic acid N-(2,6-dimethyl-cyclohexyl)-amide,
2-Thiocyanato-benzoic acid N-(2,6,6-trimethyl-cyclohexyl)-amide,
2-Thiocyanato-benzoic acid N-(3-isopropyl-5-methyl-cyclohexyl)-amide,
2-Thiocyanato-benzoic acid N-(3-isopropyl-6-methyl-cyclohexyl)-amide,
2-Thiocyanato-benzoic acid N-(2,4,6-trimethyl-cyclohexyl)-amide,
2-Thiocyanato-benzoic acid N-(4-propyl-cyclohexyl)-amide,
2-Thiocyanato-benzoic acid N-(3-isopropyl-cyclohexyl)-amide,
2-Thiocyanato-benzoic acid N-(4-cyclohexylmethyl-cyclohexyl)-amide,
2-Thiocyanato-benzoic acid N-(3-cyclohexyl-cyclohexyl)-amide,
2-Thiocyanato-benzoic acid N-(4-cyclohexyl-cyclohexyl)-amide,
2-Thiocyanato-benzoic acid N-(2-cyclohexyl-cyclohexyl)-amide and
2-Thiocyanato-benzoic acid N-(2-isopropyl-5-methyl-cyclohexyl)-amide.

The preparation of the compounds of the formula (I) according to the invention can be illustrated by the following equation, where, for example, 2-mercaptobenzoic acid N-(2-ethyl-cyclohexyl)-amide and cyanogen chloride are used as starting substances:

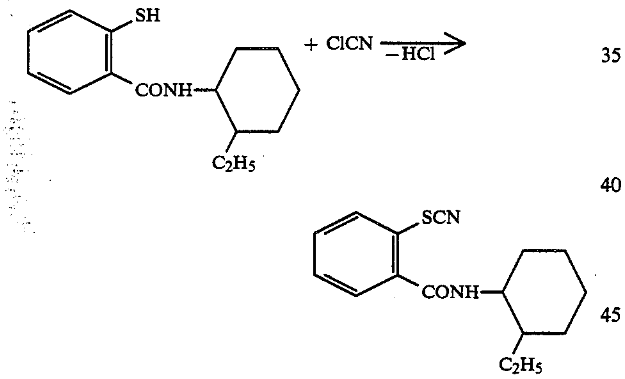

Formula (II) provides a general definition of the 2-mercaptobenzoic acid amides to be used as starting compounds. The compounds are known and/or can be prepared by known processes.

Thus, for example, they can be synthesized in the following way: starting from diphenyldisulphide-2,2'-dicarboxylic acid and thionyl chloride, the di-acid chloride is prepared, and is reacted with a primary amine to give the corresponding diphenyldisulphide-2,2'-dicarboxylic acid amide. The 2-mercaptobenzoic acid amides can be prepared therefrom by reduction, for example with zinc powder.

The cyanogen halides of the formula (II) also to be used as starting substances are generally known compounds.

The reaction of the 2-mercaptobenzoamides with the cyanogen halide is preferably carried out in the presence of a diluent. Possible diluents are virtually all the inert organic solvents. These include, in particular, alcohols, such as, for example, methanol and ethanol; nitriles, such as acetonitrile; aromatics, such as toluene; ethers, such as tetrahydrofuran, glycol dimethyl ether and dioxane; and amides, such as dimethylformamide and N-methylpyrrolidinone. It is also possible to use mixtures of diluents, such as, for example, two-phase mixtures of an aromatic and water.

The reaction temperature can be varied within a wide range. The reaction is usually carried out between −40° C. and +60° C., preferably between −20° C. and +40° C.

If appropriate, the reaction can be carried out in the presence of a base. Suitable bases are alkali metal and alkaline earth metal hydroxides, such as sodium hydroxide, potassium hydroxide, magnesium hydroxide and barium hydroxide, and alkali metal carbonates, such as sodium carbonate and potassium carbonate; and tertiary amines, such as triethylamine, dimethyl-benzylamine and 1,4-diaza-bicyclo(2,2,2)octane. The amount of base in relation to the mercapto-benzamide can be 0.1 to 100 mol %. However, it is also possible to carry out the reaction in the presence of acid catalysts; possible acid catalysts are: mineral acids, such as hydrochloric acid and sulphuric acid; and carboxylic acids, such as acetic acid.

The amount of acid catalyst in relation to the mercapto-benzamide can be 0.1 to 20 mol %.

The mercapto-benzamide and the cyanogen halide are in general used in equimolar amounts. However, it may be advantageous, especially if cyanogen chloride is used, for this to be employed in excess. The excess can be up to 20 times in relation to the mercapto-benzamide.

The active compounds according to the invention exhibit a powerful microbial action and can be employed in practice for combating undesired micro-organisms. The active compounds are suitable for use as plant protection agents.

Thus, for example, fungicidal agents in plant protection can be employed for combating Plasmodiophoromycetes, Oomycetes, Chytridiomycetes, Zygomycetes, Ascomycetes, Basidiomycetes and Deuteromycetes.

A few causative organisms of fungal diseases, which fall under the headings listed above, may be mentioned by way of example but without imposing restrictions:

*Botrytis* species, such as, for example, *Botrytis cinerea;*
*Plasmopara* species, such as, for example *Plasmopara viticola,*
*Uromyces* species, such as, for example *Uromyces appendiculatus;*
*Sphaerotheca* species, such as, for example, *Sphaerotheca fuliginea;*
*Venturia* species, such as, for example, *Venturia inaequalis;*
*Podosphaera* species, such as, for example, *Podosphaera leucotricha;*
*Phytophthora* species, such as, for example, *Phytophthora infestans;*
*Erysiphe* species, such as, for example, *Erysiphe graminis;*
*Puccinia* species, such as, for example, *Puccinia recondita;*
*Fusarium* species, such as, for example, *Fusarium culmorum;*
*Ustilago* species, such as, for example, *Ustilago nuda* or *avenae,*
*Septoria* species, such as, for example, *Septoria nodorum;*
*Tilletia* species, such as, for example, *Tilletia caries;*

*Pyricularia* species, such as, for example, *Pyricularia oryzae;*

*Pellicularia* species, such as, for example, *Pellicularia sasakii;*

*Pyrenophora* species, such as, for example, *Pyrenophora teres* (Conidia form: *Drechslera,* syn: *Helminthosporium*);

*Leptosphaeria* species, such as, for example, *Leptosphaeria nodorum,*

*Cochliobolus* species, such as, for example, *Cochliobolus sativus* (Conidia form: *Drechslera,* syn: *Helminthosporium*); and

*Cercospora* species, such as, for example, *Cercospora canescens.*

The good toleration by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and an-ionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussion Blue, and organic dyestuffs, such as alizarin dyestuffs, azo dyestuffs and phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and as a mixture with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 kg per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

When used appropriately, some of the compounds are also effective against rice diseases (*Pyricularia oryzae*) and have a good action in the in-vitro plate test; the good action against a very large variety of cereal diseases may be mentioned.

The process according to the invention is illustrated by the following preparation examples, but is not limited to these.

PREPARATION EXAMPLES

Example 1

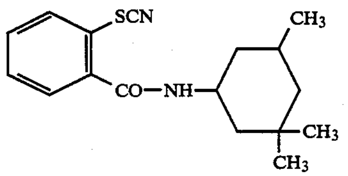

49.9 g (0.18 mol) of 2-mercaptobenzoic acid N-(3,5,5-trimethyl-cyclohexyl)-amide are initially introduced into 200 ml of tetrahydrofuran. The solution is cooled to −15° C. and 33.3 g (0.54 mol) of cyanogen chloride, dissolved in 50 ml of tetrahydrofuran, are added dropwise in the course of 30 minutes such that the internal temperature does not exceed −5° C. When the dropwise addition has ended, the mixture is allowed to come to room temperature in the course of 1 hour and stirring is then continued at this temperature for a further 2 hours. Excess cyanogen chloride and some of the solvent are distilled off under reduced pressure. The solution is poured into water, with vigorous stirring, and the solid which has precipitated is filtered off with suction and dried in a desiccator. 47 g (86.5% of theory) of 2-thiocyanato-benzoic acid N-(3,5,5-trimethylcyclohexyl)-amide are obtained as a colorless powder of melting point 117° C.

| Elemental analysis: | C | H | N |
|---|---|---|---|
| calculated: | 67.51 | 7.33 | 9.26 |
| found: | 67.6 | 7.3 | 9.3 |

The compounds of the formula (I) were obtained in the same way:

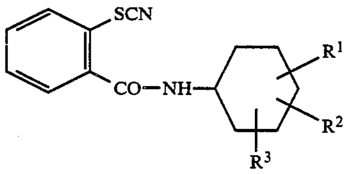

| Example | $R^3$ | $R^2$ | $R^1$ | Melting point (°C.) | Yield (% of theory) |
|---|---|---|---|---|---|
| 2 | 2-$CH_3$ | H | H | 151-3 | 89.1 |
| 3 | 3-$CH_3$ | H | H | 128-30 | 79.8 |
| 4 | 4-$CH_3$ | H | H | 124-6 | 82 |

Use examples

The compounds shown below are used as comparison substance in the use examples which follow:

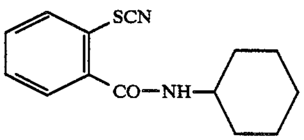

(A)

2-Thiocyanato-benzoic acid N-cyclohexyl-amide

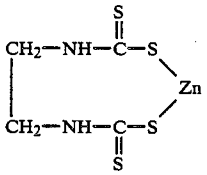

(B)

Zinc ethylene-1,2-bis-dithiocarbamate

Example A

Venturia test (apple)/protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to preparation Examples 1 and 2.

Example B

Phytophthora Test (tomato)/curative

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous spore suspension of *Phytophthora infestans.* The plants remain in an incubation cabinet at 20° C. and 100% relative atmospheric humidity for 7 hours. After a short drying off time, the plants are sprayed with the preparation of active compound until dripping wet.

The plants are placed in an incubation cabinet at 100% relative atmospheric humidity and at about 20° C.

Evaluation is carried out 3 days after the inoculation.

In this test, a clearly superior activity compared with the prior art is shown, for example, by the compounds according to preparation Examples 1 and 2.

Example C

Erysiphe test (barley)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. *hordei.*

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the following preparation Examples 1 and 4.

Example D

Leptosphaeria nodorum test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum.* The plants remain for 48 hours in an incubation cabinet at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compounds according to the following preparation examples: 1 and 4.

It will be understood that the specification and examples are illustrative but not limitative of the present invention and that other embodiments within the spirit and scope of the invention will suggest themselves to those skilled in the art.

We claim:

1. A 2-thiocyanato-benzamide of the formula

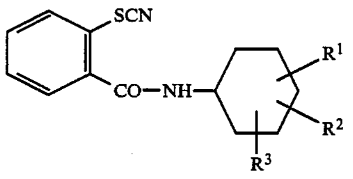

in which $R^1$, $R^2$ and $R^3$ are identical or different and represent straight-chain, branched or cyclic alkyl radical with up to 8 carbon atoms, a phenyl-alkyl radical which has 1 to 4 carbon atoms in the alkyl radical and is optionally mono-, di-, tri-, tetra- or penta-substituted by alkyl with 1 to 4 carbon atoms, or a cycloalkyl-alkyl radical with 5 to 8 carbon atoms in the cycloalkyl part and 1 to 4 carbon atoms in the alkyl part, or $R^1$ and $R^2$ independently of one another represent hydrogen.

2. A 2-thiocyanato-benzamide according to claim 1, in which $R^1$, $R^2$ and $R^3$ are identical or different and represent straight-chain or branched alkyl with 1 to 4 carbon atoms, cycloalkyl with 5 to 8 carbon atoms or phenylmethyl, phenylethyl, cyclohexylmethyl or cyclohexylethyl, each of which is optionally mono-, di- or tri-substituted by identical or different substituents from the group comprising methyl and ethyl, or $R^1$ and $R^2$ independently of one another represent hydrogen.

3. A 2-thiocyanato-benzamide according to claim 1, in which $R^1$, $R^2$ and $R^3$ are identical or different and represent methyl, ethyl, n- or iso-propyl, cyclohexyl, or benzyl or cyclohexylmethyl, each of which is optionally mono- or di-substituted by methyl, or $R^1$ and $R^2$ independently of one another represent hydrogen.

4. A compound according to claim 1, wherein such compound is 2-thiocyanato-benzoic acid N-(3,5,5-trimethylcyclohexyl)-amide of the formula

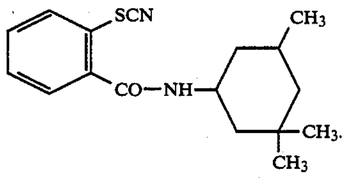

5. A compound according to claim 1, wherein such compound is 2-thiocyanato-benzoic acid N-(2-methylcyclohexyl)-amide of the formula

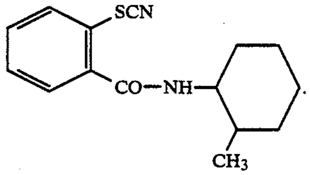

6. A compound according to claim 1, wherein such compound is 2-thiocyanato-benzoic acid N-(3-methylcyclohexyl)-amide of the formula

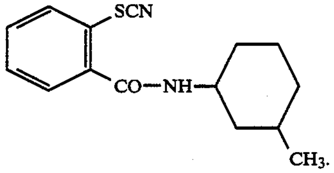

7. A compound according to claim 1, wherein such compound is 2-thiocyanato-benzoic acid N-(4-methylcyclohexyl)-amide of the formula

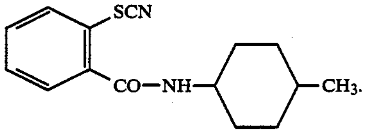

8. A fungicidal composition comprising a fungicidally effective amount of a compound according to claim 1 in admixture with a diluent.

9. A method of combating fungi which comprises administering to such fungi or to a fungus habitat a fungicidally effective amount of a compound according to claim 1.

10. The method according to claim 9, wherein such compound is 2-thiocyanato-benzoic acid N-(3,5,5-trimethylcyclohexyl)-amide, 2-thiocyanato-benzoic acid N-(2-methylcyclohexyl)-amide, 2-thiocyanato-benzoic acid N-(3-methylcyclohexyl)-amide or 2-thiocyanato-benzoic acid N-(4-methylcyclohexyl)-amide.

* * * * *